(12) United States Patent
Wedel

(10) Patent No.: US 7,831,023 B2
(45) Date of Patent: Nov. 9, 2010

(54) X-RAY DIAPHRAGM

(75) Inventor: Matthias Wedel, Nürnberg (DE)

(73) Assignee: Siemens Aktiengesellschaft (DE)

( * ) Notice: Subject to any disclaimer, the term of this patent is extended or adjusted under 35 U.S.C. 154(b) by 196 days.

(21) Appl. No.: 12/104,124

(22) Filed: Apr. 16, 2008

(65) Prior Publication Data

US 2008/0285718 A1 Nov. 20, 2008

(30) Foreign Application Priority Data

Apr. 24, 2007 (DE) .................... 10 2007 019 334

(51) Int. Cl.
*G21K 1/04* (2006.01)
*G21K 1/02* (2006.01)

(52) U.S. Cl. ...................... 378/150; 378/148

(58) Field of Classification Search .......... 378/145–160
See application file for complete search history.

(56) References Cited

U.S. PATENT DOCUMENTS

| | | | |
|---|---|---|---|
| 4,741,009 A * | 4/1988 | Yamagata et al. .......... 378/98.4 |
| 5,008,911 A | 4/1991 | Harding |
| 5,231,652 A | 7/1993 | Harding |
| 5,287,396 A * | 2/1994 | Stegehuis .................. 378/98.2 |
| 5,563,924 A | 10/1996 | Winkelmann |
| 7,272,208 B2 * | 9/2007 | Yatsenko et al. ............ 378/145 |
| 2003/0219092 A1 * | 11/2003 | Bressel et al. ................. 378/4 |
| 2006/0050841 A1 | 3/2006 | Distler et al. |
| 2006/0262897 A1 | 11/2006 | Raupach |

FOREIGN PATENT DOCUMENTS

DE 199 62 281 A1 6/2001
DE 10 2005 018 811 A1 11/2006

OTHER PUBLICATIONS

Hungarian Search Report dated Nov. 3, 2008 for Hungarian Patent Application P 0800265.
German Office Action dated Mar. 3, 2008 with English translation.

* cited by examiner

*Primary Examiner*—Irakli Kiknadze
(74) *Attorney, Agent, or Firm*—Brinks, Hofer, Gilson & Lione

(57) ABSTRACT

A diaphragm system for an x-ray apparatus for scanning an object is provided. The diaphragm system includes a diaphragm support arranged within a radiation path of an x-ray beam. The diaphragm support includes at least two different individual diaphragms. The at least two different individual diaphragms may be controlled as a function of a definable radiation intensity and/or the size of a surface of the object to be irradiated and can be introduced into the radiation path.

31 Claims, 2 Drawing Sheets

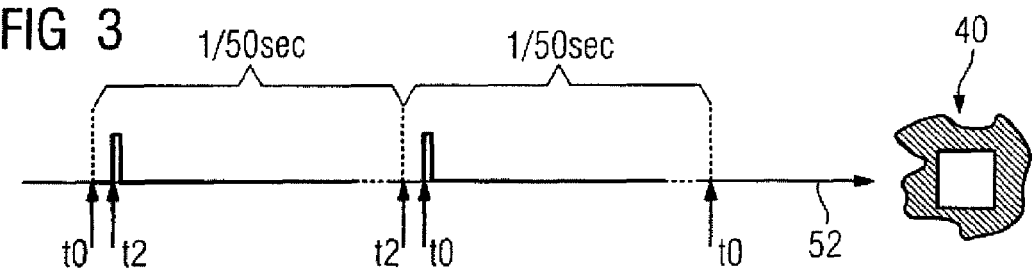
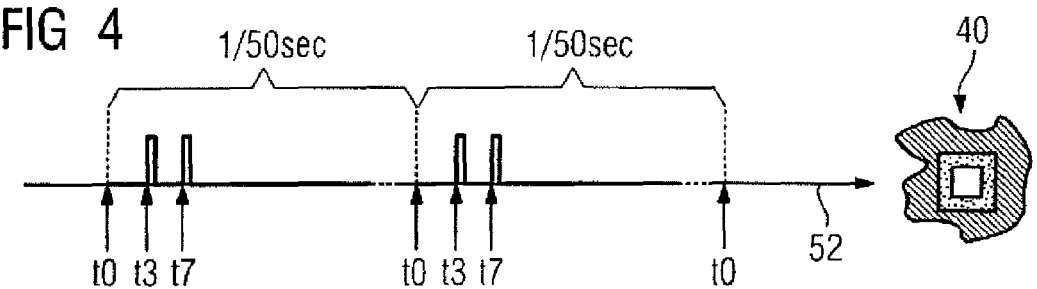
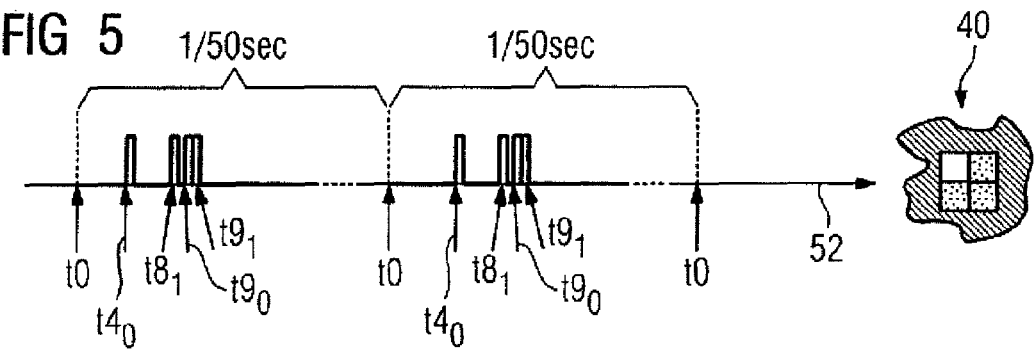

X-RAY DIAPHRAGM

This application claims the benefit of DE 10 2007 019 334.5 filed Apr. 24, 2007, which is hereby incorporated by reference.

BACKGROUND

The present embodiments relate to a diaphragm for an x-ray apparatus.

A patient may be continuously x-rayed during a medical treatment and/or medical intervention, such as an endoscopic intervention. The patient is exposed to ionizing and potentially harmful radiation. High exposure doses may lead to radiation injury after longer treatments or interventions, for example, in the head region and in the brain. The radiation injury may result in reddening of the skin or cause tissue damage. A treating physician and the medical support personnel are also exposed to continuous scattered radiation during the treatment, since they are close to the patient during the endoscopic intervention. Accordingly, a reduction to the exposure dose for each party is desired The strategies used to prevent unnecessarily high exposure allow for a partial acceptance of the radiation injury in consideration of the medical benefits. A reduction in the radiation dose is however to be achieved as far as possible. The radiation dose cannot be reduced arbitrarily, since the image quality which is essential to the examinations suffers as a result. A further possibility of reducing the overall exposure dose consists in restricting the effective field of view by more or less statically inserted diaphragms. These diaphragms can be controlled using suitable mechanisms.

A dynamic shadowing effect of certain regions of the radiation path prevents surrounding tissue from being damaged during the radiation and/or x-ray process.

DE 10 2005 018 811 A1 discloses a diaphragm apparatus for an x-ray apparatus provided to scan an object. The diaphragm apparatus includes at least two diaphragms, with a bundle of rays set with the first diaphragm being at least partially dynamically masked by the second diaphragm for at least one segment of the scanning. The radiation dose for an object is reduced, such that a precise setting of the bundle of rays for illuminating the measurement field of a detector and also a dynamic masking of an unnecessary part of the x-rays can be carried out using the diaphragm apparatus. This dynamic masking of a part of the x-rays is implementable at high speed.

SUMMARY AND DESCRIPTION

The present embodiments may obviate one or more of the drawbacks or limitations inherent in the related art. For example, in one embodiment, a diaphragm support system reduces the radiation dose for an object during the scanning process.

In one embodiment, an x-ray apparatus for scanning an object may include a diaphragm facility. The x-ray apparatus may be an x-ray diagnosis device including an x-ray source and an x-ray detector. The x-ray apparatus includes a support system in a radiation path of an x-ray beam. The diaphragm support may be equipped with at least two different individual diaphragms. The at least two individual diaphragms may be controllable as a function of a definable radiation intensity and/or the size of a surface of the object to be irradiated and to be insertable into the radiation path. Different individual diaphragms may include diaphragm openings with different radiation permeability. The diaphragms may include diaphragm openings of a different size.

Different individual diaphragms may have diaphragm openings with inlays of different material thicknesses. The different individual diaphragms may have diaphragm openings with inlays made of different materials. Different intensities may be selected for different regions, which are subjected to x-rays. The overall radiation dose for the patient may be significantly reduced during an operative intervention. The observation intensity may be reduced for less important and/or border areas, which results in the radiation intensity in these regions being reduced. This reduction in the radiation dose may be achieved by a reduced diaphragm opening and/or by different shielding materials within the diaphragm opening.

The entire region of the x-ray field is not always of equal interest to the observer, for example, a radiologist. Parts of the field of view and/or observation area do not or only insignificantly change over certain periods of time, so that they do not have to be continuously x-rayed with the highest resolution and with a maximum radiation intensity.

In one embodiment, at least two individual diaphragms are arranged next to one another on the moveable diaphragm support. The diaphragm support may be moveable in a translatory and/or rotary manner. The diaphragm support may be, for example, a rotating circular disk with individual diaphragms distributed across several circular segments. The diaphragm support may be moved quickly (e.g., rotated). The selected openings and/or inserts as diaphragms for the x-ray process leave a certain region of the field that is irradiated by the x-ray emitter open and/or attenuate the field in a desired manner. If the correct opening of the moving and/or moveable diaphragm support is in the radiation path, a radiation pulse is triggered. Only the regions not attenuated by the diaphragm can irradiate the body with full intensity.

In one embodiment, each individual diaphragm includes a contour of a rectangle. The resulting opening of each individual diaphragm with an inlay may have the contour of a rectangle. The diaphragm support and/or the inlays for the individual diaphragms may be manufactured from flat material. The introduction of different openings into the moveable and/or moving templates allows the desired regions in the actual radiation path to be irradiated. The disk and/or template itself can be manufactured, for example, from a material which is largely impermeable to x-rays, such as a lead alloy. By introducing different inserts into the moving template, which can be manufactured from sheet copper of a suitable thickness, for example, regions in the radiation path can be x-rayed with a different intensity.

More complex radiation profiles can also be realized by combining different openings during a passage of the templates, e.g. a central region with high radiation and a very good resolution and a peripheral region with a reduced dose and lower resolution.

An x-ray apparatus for scanning an object may include an x-ray source and an x-ray detector, having a controllable diaphragm support arranged within a radiation path of an x-ray beam. The x-ray apparatus may be an x-ray diagnosis device. The diaphragm support may include a drive, such as an electromotive drive t. The drive may introduce the desired individual diaphragm into the x-ray beam path.

An image processing system may control an x-ray apparatus. For example, if the image processing system is able to identify image areas that do not change or only change slightly, it can obtain control parameters for the x-ray apparatus. Using the image processing system may reduce the overall radiation dose for the patient to be treated. A control unit may supply a control signal to select an individual diaphragm. The control unit may be coupled to the x-ray detector, which supplies an item of image information relating to the object. The control unit may be coupled to and control the x-ray source. The x-ray source may be controlled as a function of the selected individual diaphragm and/or an item of image information relating to the object and provided by the x-ray detector.

These features allow an overall intensity of the x-rays acting on the object to result from a pulse duration of a radiation pulse and/or of several consecutive radiation pulses and/or of the radiation permeability of the individual diaphragms selected in each instance. A sequence of individual diaphragm settings can preferably be selected by the control unit, with the sequence of identical or different individual diaphragm settings being calculable from a desired overall intensity of the x-rays acting on the object. In addition, an item of image information relating to a temporal rate of change of individual image regions and supplied by the x-ray detector can be analyzed and used for the specification of a radiation intensity which can be adjusted to the temporal rate of change by means of the diaphragm facility. The parameters of the x-ray apparatus are expediently selected such that the predetermined radiation intensity correlates with the temporal rate of change of the image information in the image regions.

The image information supplied by the x-ray detector may have predeterminable image repetition rates and may be separated into different image regions, which indicate significantly different rates of change between consecutive items of image information. The areas that correspond to image regions with high rates of change between consecutive items of image information may be subjected to a high radiation intensity. Those image regions with low rates of change between consecutive items of image information may be exposed to a low radiation intensity. The image regions with low rates of change may be exposed to lower radiation intensity than the areas that correspond to image regions with high rates of change.

Different regions in the radiation path of an x-ray emitter may be masked or x-rayed with a reduced dose using the x-ray apparatus, which has a diaphragm facility. The different radiation profiles may be individually selected at a very high speed for each individual image during the x-ray process (e.g., approximately 50 to 60 images per second). A stepper motor may, for example, drive the diaphragm facility. An electromotive drive may be provided without levels, provided the precise synchronization of the diaphragm settings with the respective pulse resolution of the x-ray generator is ensured under all circumstances. The position of the diaphragm may also be detected by markers on the rotating circular disk.

A method for generating an item of image information relating to an object by an x-ray apparatus is provided. The method includes selecting a sequence of individual diaphragm settings that define an overall intensity of the x-rays acting on the object. Each individual diaphragm is x-rayed by a radiation pulse or several radiation pulses following its selection. The sequence of individual diaphragm settings may be iteratively determined again and stipulated on the basis of a desired overall intensity of the x-rays. An item of image information relating to the temporal rate of change of individual image regions may be analyzed by an x-ray detector, so that a radiation intensity adjusted to the temporal rate of change may be predetermined by the diaphragm facility. The predetermined radiation intensity may correlate with the temporal rate of change of the image information in the image regions. Image regions may be first detected with a high rate of change, so that the detected measurement ranges of high rates of change are subjected to a high radiation intensity. The method is able to identify the regions of the image that change (or change significantly). Only the regions that change (or change significantly) need to be x-rayed with a high radiation dose. Regions, which do not change or change slightly, do not need to be fully x-rayed. A reduced image quality with lower resolution is sufficient at least temporarily for regions that do not change or change slightly. An x-ray image previously determined with a higher resolution may be used and indicated over a certain period.

In one embodiment, an x-ray therapy device may include an x-ray apparatus for therapeutically irradiating patients. A diaphragm system may control individual settings and variations of the radiation intensities, such that the regions to be irradiated either vary or can be subjected to different radiation intensities in a finely graded fashion.

BRIEF DESCRIPTION OF THE DRAWINGS

FIG. 3 shows one embodiment of an x-ray process using full radiation intensity.

FIG. 4 shows one embodiment of an x-ray process using graduated radiation intensity.

FIG. 5 shows one embodiment of an x-ray process using reduced radiation intensity.

DETAILED DESCRIPTION

Figure 1:
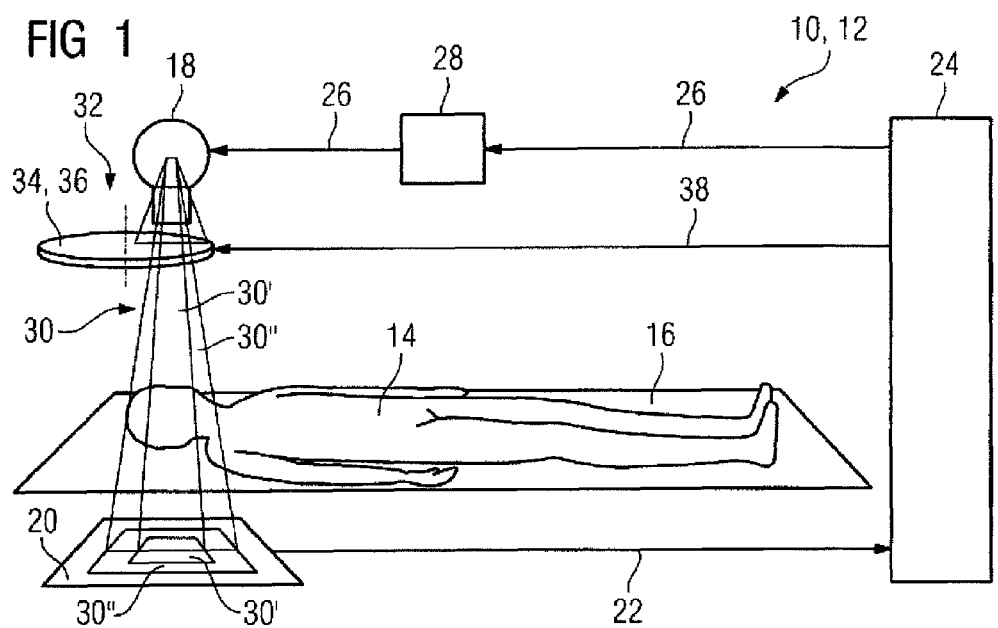
FIG. 1 shows one embodiment of a treatment facility that includes an x-ray apparatus with an adjustable diaphragm.

FIG. 1 shows an x-ray apparatus 10 as an example of an x-ray diagnosis device 12. The x-ray diagnosis device 12 scans an object, for example, a patient 14. The patient may be lying on his/her back on a patient support 16. The x-ray apparatus 10 may include an x-ray source 18, which is positioned above the head of the patient 14, and an x-ray detector 20, which is positioned below the support 16. The x-ray detector 20 supplies image information 22 to a central control unit 24. The central control unit 24 supplies a control signal 26 to an x-ray generator 28, which controls the x-ray source 18. An adjustable diaphragm system 32 is arranged below the x-ray source 18 and in the radiation path 30. The diaphragm support system 32 may include a disk-like x-ray diaphragm 34. Several individual diaphragms may be provided in a disk-like and rotatably mounted diaphragm support 36. By selecting a suitable individual diaphragm in the diaphragm support 36 using a control signal 38 from the central control unit 24, the radiation path 30 may be changed and/or divided into different image regions 30' and 30". The image regions 30' and 30" produce image regions 30' and 30" on the x-ray detector 20.

Figure 2:
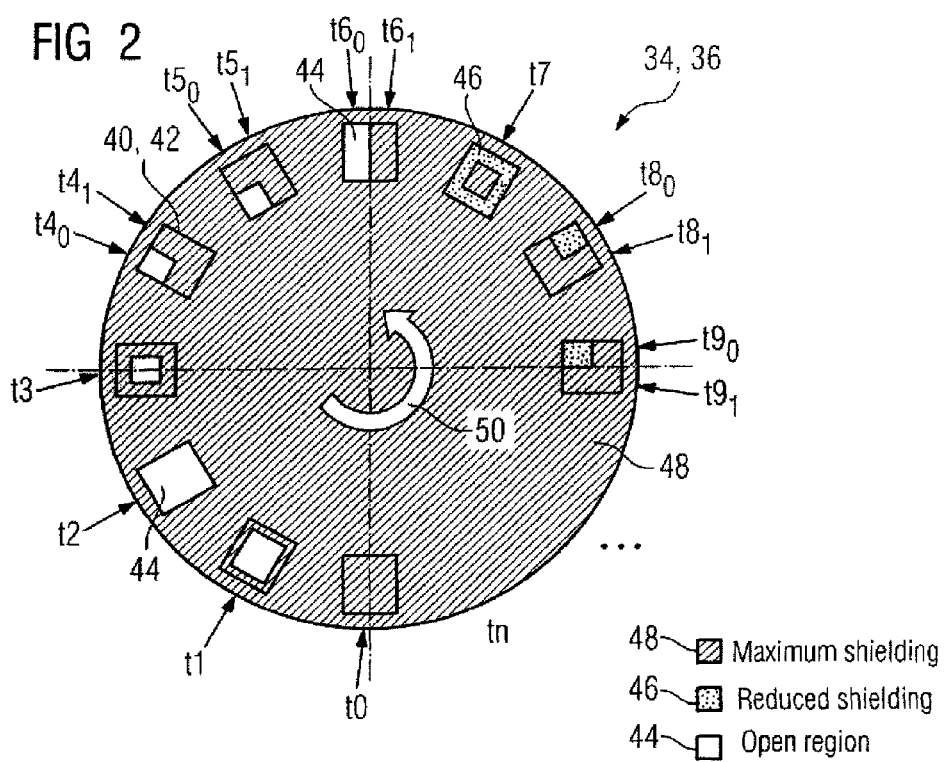
FIG. 2 shows one embodiment of a template, which forms part of a diaphragm system according to FIG. 1.

FIG. 2 illustrates one embodiment of the x-ray diaphragm 34 and/or of the disk-like diaphragm support 36. The diaphragm support 36 may include individual diaphragms 40 arranged at equal distances from one another on the outer peripheral region of the diaphragm support 36. The individual diaphragms include rectangular contours 42. As shown in FIG. 2, white fields illustrate open regions 44. Reduced shielding regions 46 are filled in with dots. Reduced shielding regions 46 may be made of, for example, sheet metal or sheet copper of a different thickness, with the material strength defining the level of the shielding. Maximum shielding regions 48 are indicated by hatching (shading) inclined to the right. The maximum shielding regions 48 relate to (cover) the overall x-ray diaphragm 34, with the exception of regions 44 and 46 within the contours 42. As shown in FIG. 2, the three different permeability regions 44, 46, 48 may be combined with one another within the individual contours 42 of individual diaphragms 42.

The different permeability regions 44, 46, 48 within the contours 42 may provide different mapping regions on the x-ray detector 20. The mapping regions may be subjected to varying radiation. The rotation direction 50 of the diaphragm support 36 defines the sequence and time instants of the radiation pulse, so that the appropriate radiation pulse corresponds to the correct position of an appropriately selected individual diaphragm 40.

FIG. 3 illustrates an embodiment where the whole area to be covered is continuously irradiated with full radiation intensity. The individual diaphragm with a fully open region 44 is selected, which is designated with $t_2$ according to FIG. 2. The required opening in the rotating disk is selected such that the radiation is triggered at exactly the time instant t, when the opening is located at the correct position in the radiation path 30. As shown in FIG. 3, in the case of full radiation along the time axis 52, starting at time instant $t_0$, the radiation pulse is then triggered if the material opening 44 is located at time instant $t_2$ within the radiation path 30.

The template (e.g., the x-ray diaphragm 34 or the disk-like diaphragm support 36) may be a rotating disk. The template includes twelve different profiles, which are configured as openings and/or as inserts in the passages. In the exemplary embodiment shown, 50 images per second of the recording region are recorded. The same profile appears again in the radiation path at 1/50 sec=20 msec, which represents the repetition rate. The radiation (within the 1/50 sec) is triggered with a total of twelve fields at 1/50/12 sec=1.6 msec. The scanning process is shortened if several profiles are used during one rotation. If one and the same profile is to be triggered a number of times, the pulse width may be lengthened by the corresponding amount.

FIG. 4 illustrates an embodiment where the center is to be subjected to full radiation intensity and the periphery to reduced radiation. The radiation intensities relate to a sequence of radiation pulses $t_3$ and $t_7$. As shown in FIG. 2, in field $t_3$ the border region is shielded and only the center is open, whereas with field $t_7$ the center is shielded and the peripheral area is provided with reduced shielding. The fields $t_3$ and $t_7$ produce the radiation intensity according to the image on the right of FIG. 4.

FIG. 5 illustrates an embodiment where the left upper region are subjected to full radiation intensity and the remaining regions are subjected to reduced radiation. A sequence of radiation pulses $t4_0$, $t8_1$, $t9_0$ and $t9_1$ correspond to fields $t_4$, $t_8$, and $t_9$. In accordance with FIG. 2, the field t4 is subdivided into the open region $t_{40}$ and the shielded region $t_{41}$. When the field $t_4$ is irradiated, the open region is irradiated according to the image on the right in FIG. 5. The irradiation of the field $t_{81}$ and the fields $t_{90}$ and $t_{91}$ according to FIG. 2 provides the desired intensity level and the desired distribution, so that the radiation intensity according to the image on the right in FIG. 5 is produced.

The present embodiments relate to a continuously rotating disk that includes individual diaphragms. The present embodiments also relate to moveable or rotatable diaphragm supports, in which the individual diaphragms are selected and remain at least temporarily in the radiation path following their selection.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A diaphragm system for an x-ray scanning system having a radiation source and an x-ray detector, the diaphragm system comprising:
    a diaphragm support arranged within a radiation path of an x-ray beam, the diaphragm support including at least two different diaphragms,
    wherein the at least two diaphragms are operable to be controlled as a function of a definable radiation intensity and/or the size of a surface of an object to be irradiated and operable to be introduced into the radiation path.

2. The diaphragm system as claimed in claim 1, wherein the at least two diaphragms have diaphragm openings of different radiation permeability.

3. The diaphragm system as claimed in claim 2, wherein the at least two diaphragms include diaphragm openings of a different size.

4. The diaphragm system as claimed in claim 2, wherein the at least two diaphragms include diaphragm openings with inlays of a different material thickness.

5. The diaphragm system as claimed in claim 2, wherein the at least two diaphragms include diaphragm openings with inlays made of different materials.

6. The diaphragm system as claimed in claim 1, wherein the at least two diaphragms are arranged next to one another on the moveable diaphragm support.

7. The diaphragm system as claimed in claim 1, wherein the diaphragm support is moveable in a translatory and/or rotatory manner.

8. The diaphragm system as claimed in claim 1, wherein the diaphragm support is a rotating circular disk with the at least two diaphragms arranged across several circular segments.

9. The diaphragm system as claimed in claim 1, wherein the at least two diaphragms include a contour of a rectangle.

10. The diaphragm system as claimed in claim 1, wherein the at least two diaphragms have an opening that includes an inlay having a contour of a rectangle.

11. The diaphragm system as claimed in claim 10, wherein the diaphragm support and/or the inlays for the at least two diaphragms are flat.

12. The diaphragm system as claimed in claim 1, wherein the x-ray scanning system is an x-ray diagnosis device and/or an x-ray therapy device.

13. An x-ray system for scanning an object, the system comprising:
    an x-ray source;
    an x-ray detector; and
    a controllable diaphragm support disposed in a radiation path of an x-ray beam, the controllable diaphragm support including at least two different diaphragms operable to be controlled as a function of a definable radiation intensity and/or the size of a surface of an object to be irradiated and operable to be introduced into the radiation path.

14. The x-ray apparatus as claimed in claim 13, wherein the diaphragm support includes a drive.

15. The x-ray apparatus as claimed in claim 14, wherein the drive includes a stepper motor.

16. The x-ray apparatus as claimed in claim 14, wherein the drive is an electromotive drive.

17. The x-ray apparatus as claimed in claim 13, wherein a control unit supplies a control signal to select one of the at least two diaphragms.

18. The x-ray apparatus as claimed in claim 17, wherein the x-ray detector is operable to provide image information, which relates to the object, to the control unit.

19. The x-ray apparatus as claimed in claim 17, wherein the control unit is operable to control the x-ray source, the x-ray source being controlled as a function of the selected diaphragm and/or image information relating to the object and supplied by the x-ray detector.

20. The x-ray apparatus as claimed in claim 13, wherein an overall intensity of the x-rays acting on the object result from a pulse duration of a radiation pulse and/or several consecutive radiation pulses and/or a radiation permeability of the selected diaphragm.

21. The x-ray apparatus as claimed in claim 13, wherein a sequence of individual diaphragm settings are selected by the control unit, the sequence of individual diaphragm settings being calculable from a desired overall intensity of radiation acting on the object.

22. The x-ray apparatus as claimed in claim 13, wherein image information relating to a temporal rate of change of individual image regions and supplied by the x-ray detector is analyzed and applied to a specification of a radiation intensity that is adjusted to the temporal rate of change by the diaphragm facility.

23. The x-ray apparatus as claimed in claim 22, wherein predetermined radiation intensity is correlated with the temporal rate of change of the image information in the image regions.

24. The x-ray apparatus as claimed in claim 23, wherein the image information supplied by the x-ray detector has predeterminable image repetition rates and is separated into different image regions, which indicate significantly different rates of change between consecutive items of image information.

25. The x-ray apparatus as claimed in claim 24, wherein an image region with a high rate of change between consecutive image information is exposed to a high radiation intensity.

26. The x-ray apparatus as claimed in claim 25, wherein an image region with a low rate of change between consecutive image information is exposed to a low radiation intensity.

27. A method for generating image information relating to an object of an x-ray apparatus, the method comprising:
    selecting a sequence of individual diaphragm settings that define at least two diaphragms that control an intensity of the x-rays acting on the object; and
    irradiating the at least two individual diaphragms using a radiation pulse or several radiation pulses.

28. The method as claimed in claim 27, further comprising:
    iteratively determining the sequence of individual diaphragm settings again; and
    stipulating the sequence of individual diaphragm settings based on a desired overall intensity of the x-rays.

29. The method as claimed in claim 28, further comprising:
    analyzing image information relating to a temporal rate of change of individual image regions with an x-ray detector; and
    adjusting a radiation intensity to the temporal rate of change predetermined by the diaphragm facility.

30. The method as claimed in claim 29, wherein the predetermined radiation intensity correlates with the temporal rate of change of the image information in the image regions.

31. The method as claimed in claim 30, characterized in that image regions are first detected with a high rate of change and that subsequently the detected measurement regions of high rates of change are subjected to a high radiation intensity.

* * * * *